US00RE36070E

United States Patent [19]

Ballini et al.

[11] E Patent Number: Re. 36,070

[45] Reissued Date of Patent: Feb. 2, 1999

[54] MICRONIZED SPRAY DEVICE

[75] Inventors: Faustino Ballini, Bovezzo; Marco Merlin, Sirmione, both of Italy

[73] Assignee: Mefar S.p.A., Bovezzo, Italy

[21] Appl. No.: 833,017

[22] Filed: Apr. 3, 1997

Related U.S. Patent Documents

Reissue of:

[64] Patent No.: 5,505,193
Issued: Apr. 9, 1996
Appl. No.: 331,828
Filed: Oct. 31, 1994

[30] Foreign Application Priority Data

Nov. 9, 1993 [IT] Italy ..... MI93 A 002385

[51] Int. Cl.[6] ..... A61M 11/00

[52] U.S. Cl. ..... 128/200.14; 128/200.11; 128/200.21

[58] Field of Search ..... 128/200.11, 200.12, 128/200.13, 200.14, 200.15, 200.21, 200.16; 604/301; 222/383.1; 239/338

[56] References Cited

U.S. PATENT DOCUMENTS

| | | | |
|---|---|---|---|
| 3,746,000 | 7/1973 | Edwards | 128/200.16 |
| 3,916,896 | 11/1975 | Ballasd | 128/200.14 |

FOREIGN PATENT DOCUMENTS

| | | | |
|---|---|---|---|
| 473 165 | 6/1947 | Belgium . | |
| 0 261 649 | 3/1988 | European Pat. Off. . | |
| 0499690 | 8/1992 | European Pat. Off. | 128/200.14 |
| 0580897 | 2/1994 | European Pat. Off. | 128/200.14 |
| 300 822 | 7/1916 | Germany . | |

*Primary Examiner*—John G. Weiss
*Assistant Examiner*—V. Srivastava
*Attorney, Agent, or Firm*—Guido Modiano; Albert Josif; Daniel J. O'Byrne

[57] ABSTRACT

Micronized spray device for washing nasal and neighboring cavities including a bell-shaped body which forms an atomization chamber on the bottom whereof there is a region for containing a washing liquid in which a spray nozzle draws; the spray nozzle is associated with a compressed-air injector and is axially aligned with the inner outlet formed by the bell-shaped body. An outer skirt furthermore surrounds the bell-shaped body and forms an outer outlet which is located at the inner outlet and forms a chamber for collecting the catarrhal material that has been detached from the nasal cavities; the chamber is connected to the outside to vent the pressure generated during expiration. The outer skirt can be arranged in a first position, in which the outer outlet is spaced from the inner outlet so as to form an interspace that is connected to the collection chamber, and in a second position, in which the outer outlet overlaps the inner outlet.

20 Claims, 2 Drawing Sheets

MICRONIZED SPRAY DEVICE

Matter enclosed in heavy brackets [ ] appears in the original patent but forms no part of this reissue specification; matter printed in italics indicates the additions made by reissue.

BACKGROUND OF THE INVENTION

The present invention relates to a micronized spray device particularly for washing nasal and neighboring cavities, which in practice are the nasal fossae, the paranasal sinuses, the rhinopharnyx, the pharynx, the auditory tube, and the middle ear.

Currently there are no devices for cleansing nasal fossae and neighboring fossae from mucopurulent secretions or scabs.

In particular, currently commercially available inhalation-therapy devices are unable to eliminate catarrhal secretions, since they produce a jet that is too finely atomized owing to their particular structure, which has obstacles, diaphragms, or bends between the pisper and the outlet: these characteristics allow to produce a very fine aerosol that is suitable to penetrate in the tracheobronchial region but loses the larger water particles that are instead useful for treating the upper respiratory tract.

SUMMARY OF THE INVENTION

A principal aim of the present invention is instead to produce an abundant aerosol with large-diameter particles that can penetrate directly in the nasal fossae, in the rhinopharynx, and in the pharynx.

Inhalation-therapy devices are furthermore unable to obtain a direct effect with penetration of the water particles in the paranasal sinuses and in the middle ear, since they are not applied with positive pressure.

An object of the present invention is instead to produce and transmit a positive pressure from the atomizing chamber to the nasal fossae so that the patient can, by swallowing, cause the micelles thus produced to penetrate in the paranasal sinuses and in the middle ear.

Another object of the invention is indeed to eliminate the above described drawbacks by providing a micronized spray device for washing nasal and neighboring cavities, in which there is a micronized jet which is directed and introduced in the nostrils without any diaphragm, obstacle, or curve that can limit its flow-rate or vary the diameter of the micelles as produced by the pisper, and the pressure whereof can furthermore be discharged completely into the nasal fossae, producing a positive-pressure space during swallowing.

Within the scope of the above specified aim, a particular object of the invention is to provide a micronized spray device that can perform a deep cleaning action that can affect the paranasal sinuses and the middle ear without however applying pressures that might be harmful.

Another object of the present invention is to provide a micronized spray device that allows to collect in a delimited region the water that returns from the nasal fossae, preventing the contamination of the physiological washing water that is atomized.

Another object of the present invention is to provide a micronized spray device which, by virtue of its particular constructive characteristics, is capable of giving the greatest assurances of reliability and safety in use.

With this aim, these objects, and others in view which will become apparent hereinafter, there is provided a micronized spray device for washing nasal cavities, according to the invention, which is characterized in that it comprises a bell-shaped body which forms an atomization chamber on the bottom of which there is a region for containing a washing liquid in which a spray nozzle draws. The spray nozzle is associated with a compressed-air injector and is axially aligned with the inner outlet formed by said bell-shaped body. An outer skirt furthermore surrounds the bell-shaped body and forms an outer outlet at the inner outlet and a second chamber which is concentric to the first one to collect the catarrhal secretions that have been detached from the nasal cavities. The second chamber is connected to the outside to vent the pressure generated during expiration. The outer skirt is arrangeable in a first position, in which the outer outlet is spaced from the inner outlet to thereby form an interspace that is connected to the collection chamber, and in a second position, in which the outer outlet overlaps the inner outlet.

BRIEF DESCRIPTION OF THE DRAWINGS

The particular characteristics and advantages of the invention will become apparent from the following detailed description of a preferred but not exclusive embodiment thereof, illustrated only by way of non-limitative example in the accompanying drawings, wherein.

DESCRIPTION OF THE PREFERRED EMBODIMENTS

Figure 1:
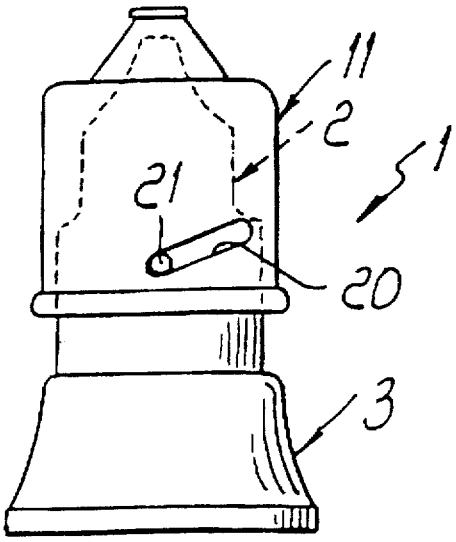
FIG. 1 is a schematic lateral elevation view of the device according to the invention.

With reference to the above figures, the micronized spray device for washing nasal cavities and neighboring cavities, according to the invention, is generally designated by the reference numeral 1 and comprises a bell-shaped body 2 which is detachably sealingly associable with a cap 3 to form an atomization chamber designated by the reference numeral 4.

At the bottom of the chamber 4 there is a region 5 that contains a washing liquid, which can be constituted by medicated or non-medicated physiological water or optionally by thermal water.

A spray nozzle, generally designated by the reference numeral 6, draws in the physiological water, has a cylindrical body 7 that is open towards the bottom, i.e. at the region 5, and has in an upward region a spraying hole 8 which is arranged at a compressed-air injector 9 which is located inside the cylindrical body 7 and forms in practice, together with the body 7, a region for aspirating the washing liquid which is injected by means of the spraying hole 8.

The particular structure that is adopted allows to create a jet of aqueous micelles whose diameter is greater than that of particles dispensed by conventional inhalation-therapy devices; a very large percentage of said micelles has a diameter of more than 10 microns, measured with a Malvern Size 2600 granulometer.

The jet of micronized aqueous particles is sent into the atomization chamber 4, which has an outlet 10 axially aligned with the spraying hole 8.

On the outside of the bell-shaped body 2 there is an outer skirt, designated by the reference numeral 11, having a lateral body 12 that is sealingly coupled externally to the bell-shaped body by virtue of the presence of an O-ring 13.

The skirt 11 forms, in an upward region, an outer outlet 15 which is arranged correspondingly and is axially aligned with the inner outlet 10.

Means are also provided for movably connecting said outer skirt 11, in an axial direction, with respect to the bell-shaped body; said means are advantageously constituted by at least one helical slot 20 which is formed on the outer skirt and in which there engages a pin 21 that protrudes from the cap 3 which is rigidly coupled to the bell-shaped body 2.

Furthermore, the outer skirt has, towards its upper part, ports 25 that connect to the outside the chamber 26 that collects the return water, which is constituted by the washing liquid and by the catarrhal material that has been detached from the nasal cavities.

There is also a pressure control valve element for discharging the excess pressure from said nebulization chamber 4; said valve element is constituted by a hole 30 which is formed in the upper part of the bell-shaped body 2 and is connected to the chamber 26.

Figure 2:
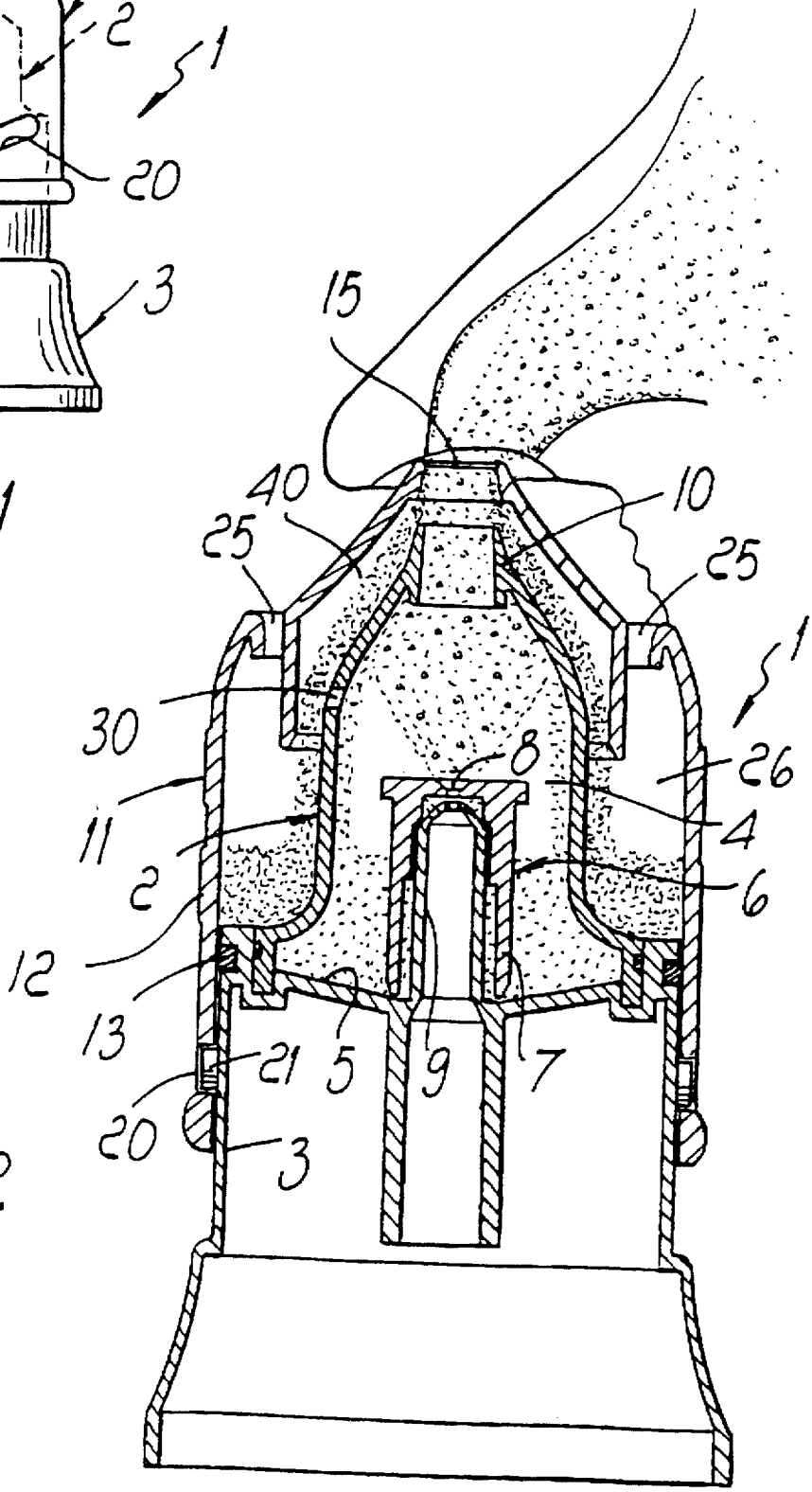
FIG. 2 is an axial sectional view of the device with the outer skirt in the first position.
Figure 3:
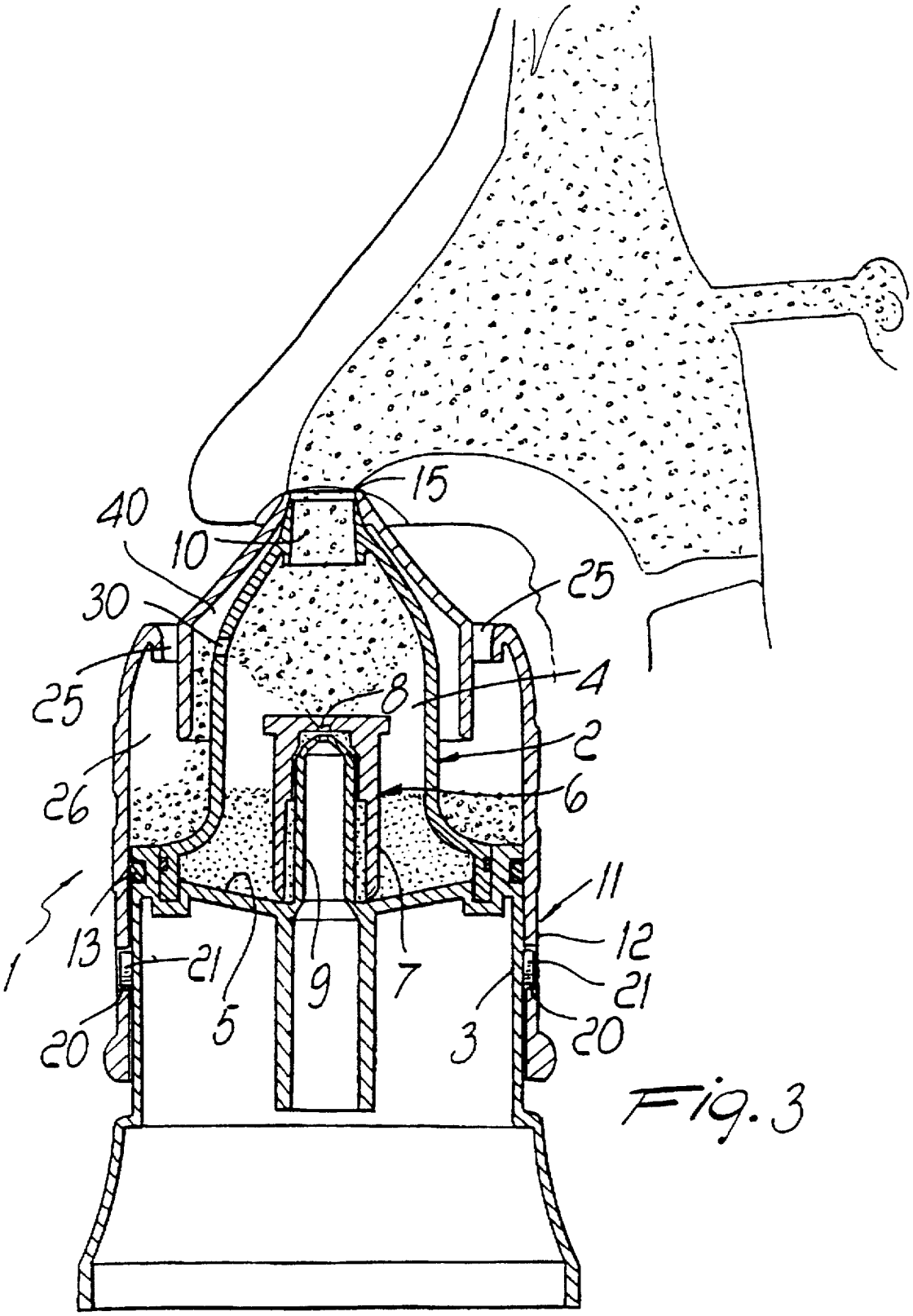
FIG. 3 is an axial sectional view of the device with the outer skirt in the second position.

The outer skirt 11 can be arranged in a first position, shown in FIG. 2, in which the outer outlet 15 is spaced from the inner outlet 10, in practice forming an interspace 40 that allows the physiological material that has been detached from the nasal cavities to pass directly inside the chamber 26, preventing said physiological material from mixing with the washing liquid provided in the region 5. The outer skirt 11 can furthermore be arranged as shown in FIG. 3, in a second position, in which the inner outlet 10 enters the outer outlet to allow to penetrate in the paranasal cavities and in the middle ear and achieve the effect of cleansing and eliminating the catarrh and/or conveying the medicated constituents contained in addition to the washing water or thermal water.

In practical operation, during a first step the outer skirt is placed in the first position; when the compressed air is introduced by means of the injector, a jet of micelles of physiological water is obtained with particles larger than 10 microns in diameter which is atomized directly in the nostrils under a certain degree of pressure.

The abundant hydration of the nasal and neighboring cavities obtained with the micronized jet dissolves mucus and catarrh and detaches them due to the pressure applied to the mucous membranes.

The removed catarrhal and scab material, dissolved in the physiological water, is deposited by gravity in the collection chamber 26 without mixing with the stream that leaves the atomization chamber 4 by virtue of the pressure that escapes from the chamber, which does not allow the mucus to fall back inside it.

The pressure generated by the respiration of the patient during expiration is mainly discharged with the contralateral nostril and partly through the interspace 40 and the ports 25 that provide a connection to the outside.

After the first above described step of washing the nasal fossae, the rhinopharynx, and the pharynx, it may be necessary to perform a second washing step to clean the paranasal sinuses and open the auditory tube, restoring their functionality and thus normalizing the pressure of the middle ear with respect to the outside.

During this second step, the outer skirt of the device is placed in the second position, so as to fully close the interspace 40.

In order to clean the paranasal sinuses and open the auditory tube, the patient must swallow as frequently as possible, for example by sucking candy.

During these swallowing actions, a positive pressure is produced inside the nasal fossae and is caused by the pressure of the atomization obtained in the chamber 4.

This positive pressure is discharged towards all the neighboring cavities, thus into the paranasal cavities, into the auditory tube, and into the middle ear.

This also causes the aqueous micelles to move towards said cavities, cleansing them by diluting the mucus, by equalizing and normalizing the internal pressure of these cavities with respect to the external pressure, and by producing the pharmacological effect of any medical or thermal substances contained in the washing liquid.

During this step it is absolutely necessary to avoid creating dangerous pressure values, since an excessive pressure might cause internal lesions.

The compressed air that generates the micronized jet is normally set to 170±10 kPa. During atomization, with the outer skirt arranged so as to fully close the interspace 40, during the swallowing actions of the patient the internal pressure increases in the atomization chamber but can partly vent by means of the safety hole 30 and partly open the auditory tubes and cause the atomized liquid to move towards the paranasal sinuses.

Furthermore, the liquid arriving from the nasal cavity and deposited in the chamber 26 is discharged through the hole 30.

The overpressure vented by virtue of the valve means constituted by the hole 30 discharges freely into the atmosphere by means of the ports 25.

From the above description it is thus evident that the invention achieves the intended aim and objects, and in particular the fact is stressed that a device is provided which, by sending into the nasal cavities an atomized jet in which a high percentage of its aqueous micelles arc over 10 microns in size, allows to perform deep washing with optimum pressure values which in any case never reach dangerous levels.

The catarrhal material that is detached from the nasal cavities is furthermore not mixed with the washing liquid, which thus always has the best characteristics.

The invention thus conceived is susceptible of numerous modifications and variations, all of which are however within the scope of the inventive concept.

All the details may furthermore be replaced with other technically equivalent elements.

In practice, the materials employed, so long as they are compatible with the specific use, as well as the contingent shapes and dimensions, may be any according to the requirements.

What is claimed is:

1. Micronized spray device for washing nasal and neighboring cavities, comprising a bell-shaped body having a bottom and an inner outlet, said bell-shaped body forming an atomization chamber on the bottom thereof for containing a washing liquid, a compressed-air injector having a spray nozzle, said spray nozzle being axially aligned with said inner outlet, an outer skirt surrounding said bell-shaped body and having an outer outlet aligned with said inner outlet, a chamber for collecting catarrhal material detached from the nasal cavities disposed between the outer skirt and said bell-shaped body, said collecting chamber having ports on the outer skirt to vent pressure generated during use to the outside of the micronized spray device, said outer skirt being movable between a first position, in which said outer outlet is spaced from said inner outlet thereby forming an interspace leading to said collecting chamber, and a second position, in which said outer outlet overlaps said inner outlet and thus closes said interspace.

2. Device according to claim 1, further comprising a cap, said bell-shaped body being sealingly and detachably connected in a lower region thereof to said cap to form said atomization chamber.

3. Device according to claim 1, wherein said spray nozzle comprises a cylindrical body that is open towards the bottom and has, in an upper region, a spraying hole.

4. Device according to claim 1, wherein a jet of aqueous micelles are produced during use, a large percentage of said aqueous micelles having a size above 10 microns.

5. Device according to claim 1, wherein said outer skirt comprises a body being sealingly coupled on the outside of said bell-shaped body.

6. Device according to claim 1, further comprising means for moving said outer skirt with respect to said bell-shaped body between said first position and said second position.

7. Device according to claim 6, wherein said moving means comprises at least one helical slot formed on said outer skirt, at least one pin protruding from said cap for engaging with said at least one helical slot.

8. Device according to claim 1, further comprising a pressure control valve element for discharging excess pressure build up in said atomization chamber.

9. Device according to claim 8, wherein said pressure control valve element is constituted by a through hole formed in said bell-shaped body for connecting said atomization chamber with said collecting chamber.

*10. Micronized spray device for delivering atomized fluid to nasal and sinus cavities, comprising:*

*a body having a bottom and an inner outlet;*

*said body forming an atomization chamber on the bottom thereof for containing a washing liquid;*

*a compressed-air injector having a spray nozzle including a spraying hole disposed within said body;*

*an outer skirt surrounding said body and having an outer outlet;*

*a chamber for collecting drainage from the nasal cavities disposed between the outer skirt and said body;*

*said collecting chamber having ports on the outer skirt to vent pressure generated during use to the outside of the micronized spray device.*

*11. Device according to claim 10, further comprising a cap, said body being sealingly and detachably connected in a lower region thereof to said cap to form said atomization chamber.*

*12. Device according to claim 10, wherein said spray nozzle comprises a cylindrical body that is open towards the bottom and said spraying hole is disposed in an upper region of said cylindrical body.*

*13. Device according to claim 10, wherein a jet of aqueous micelles are produced during use, a very large percentage of said aqueous micelles having a size of more than 10 microns.*

*14. Device according to claim 10, wherein said outer skirt comprises a body being sealingly coupled on the outside of said body.*

*15. Device according to claim 10, further comprising means for moving said outer skirt in an axial direction with respect to said body.*

*16. Device according to claim 15, wherein said moving means comprises at least one slot formed on said outer skirt, at least one pin protruding from said cap for engaging with said at least one slot.*

*17. Device according to claim 10, further comprising a pressure control valve element for discharging excess pressure build up.*

*18. Device according to claim 17, wherein said pressure control valve element is constituted by a through hole formed in said body for connecting said atomization chamber with said collecting chamber.*

*19. Device according to claim 10, wherein said body is bell-shaped.*

*20. Device according to claim 11, wherein said outer skirt is movable between a first position, in which said outer outlet is spaced from said inner outlet thereby forming an interspace leading to said collecting chamber, and a second position, in which said outer outlet overlaps said inner outlet and thus closes said interspace.*

* * * * *